United States Patent [19]
Smith et al.

[11] Patent Number: 5,886,186
[45] Date of Patent: Mar. 23, 1999

[54] SYNTHESIS OF SUBSTITUTED N-HETEROAROMATIC COMPOUNDS AND METHODS OF USE THEREOF

[75] Inventors: Robert L. Smith, Lansdale, Pa.; Gnanasambandam Kumaravel, Shrewsbury, Mass.; Donald E. Kuhla, Doylestown, Pa.

[73] Assignee: Versicor, Inc., Marlborough, Mass.

[21] Appl. No.: 548,009

[22] Filed: Oct. 25, 1995

[51] Int. Cl.$^6$ .................................................. C07D 211/72
[52] U.S. Cl. ..................... 546/311; 546/330; 546/334; 546/341; 546/345; 546/346; 546/386
[58] Field of Search .................. 546/386, 311, 546/330, 334, 341, 345, 346

[56] References Cited

U.S. PATENT DOCUMENTS

| | | | |
|---|---|---|---|
| 3,495,969 | 2/1970 | Driscoll ........................................ | 71/94 |
| 5,073,636 | 12/1991 | Humphreys et al. .................... | 546/345 |
| 5,118,766 | 6/1992 | Hendy et al. ............................ | 525/535 |
| 5,145,601 | 9/1992 | Otterholm et al. ................. | 252/299.61 |
| 5,185,339 | 2/1993 | Pilkington et al. ...................... | 514/256 |
| 5,432,175 | 7/1995 | Piwinski et al. ......................... | 514/252 |
| 5,438,033 | 8/1995 | Drumm et al. .......................... | 504/130 |

FOREIGN PATENT DOCUMENTS

94/08051   4/1994   WIPO .

OTHER PUBLICATIONS

Hodge et al., *Polymer–supported Reactions in Organic Synthesis*, John Wiley & Sons, New York, 1980, Ch. 1.
Katritzky et al., "The Preparation of Heteroaromatic N–Oxides," *Chemistry of the Heterocyclic N–Oxides*, Academic Press, New York, 1971, Ch. II, pp. 21–69.
Katritzky et al., "Reactions at N–Oxide Rings," *Chemistry of the Heterocyclic N–Oxides*, Academic Press, New York, 1971, Ch. III, pp. 142–333.
Gordon et al., "Applications of Combinatorial Technologies to Drug Discovery. 2. Combinatorial Organic Synthesis, Library Screening Strategies, and Future Directions," *Journal of Medicinal Chemistry*, vol. 37, No. 10, May 13, 1994.
Hobbs DeWitt et al., "Diversomers: An approach to non-peptide, nonoligomeric chemical diversity," *Proc. Natl. Acad. Sci. USA*, vol. 90, Aug. 1993, pp. 6909–6913.
Houghten et al., "Generation and use of synthetic peptide combinatorial libraries for basic research and drug discovery," *Nature*, vol. 354, 1991, pp. 84–86.
Atreya et al., "Interaction of Prolyl 4–Hydroxylase with Synthetic Peptide Substrates" *J. Biol. Chem.*, vol. 266, No. 5, Feb. 15, 1991, pp. 2852–2858.
Rhoades et al., "Collagen Proline Hydroxylase (Rat Skin)," *Methods in Enzymology XVIIB*, 1971, pp. 306–316.
Kivrikko et al., "Hydroxylation of Proline in Synthetic Polypeptides with Purified Protocollagen Hydroxylase," *J. Biol. Chem.*, vol. 242, No. 18, Sep. 25, 1967, pp. 4007–4012.
Halme et al., "Isolation and Partial Characterization of Highly Purified Protocollagen Proline Hydroxylase," *Biochim. Biophys. Acta*, vol. 198, 1970, pp. 460–470.
Norris et al., "The use of an in vitro binding assay to predict histamine $H_2$–antagonist activity," *Agents and Actions*, vol. 16, 1985, pp. 170–172.
Hamana et al., "Studies on Tertiary Amine Oxides. XXXVI. Reactions of Aromatic N–Oxides with 1–Morpholinoisobutene in the Presence of Acylating Agents," *Yakugaku Zasshi [Journal of the Pharmaceutical Society of Japan]*, vol. 89, No. 5, May 1969.
Hamana et al., "Reactions of Aromatic N–Oxides with Enamines of Cyclohexanone in the Presence of Acylating Agents (3). Reactions of Chloro–and Hydroxy–pyridine and –quinoline N–Oxides," *Chem. Pharm. Bull.*, vol. 15(4), 1967, pp. 474–480.
Hamana et al., "Studies on Tertiary Amine Oxides. XXXI. Reactions of Aromatic N–Oxides with Antipyrine in the Presence of Acylating Agents," *Chem Pharm. Bull.*, vol. 15(9), 1967, pp. 1380–1384.
Hamana et al., "Studies on Tertiary Amine Oxides. XXIV. Reactions of Aromatic N–Oxides with Enamines of Cyclohexanone in the Presence of Acylating Agents," *Chem. Pharm. Bull.*, vol. 13(8), 1965, pp. 912–920.
"Reaction of Aromatic N–Oxides with Indoles in the Presence of an Acylating Agent" *Chem. Pharm. Bull.*, vol. 15(3), 1967, pp. 363–366.
"Regiospecific Amination of 3–Substituted Pyridines Using Imidoyl Chloride Functionalized Polystyrene," Abramovitch et al, *Heterocycles*, 26(8), 1987.
Viktor Krchnak, et al., "Polymer–Supported Mitsunobu Ether Formation and its Use in Combinatorial Chemistry", *Tetrahedron Letters*, vol. 36, No. 35, pp. 6193–6196 (1995).
Hervé Deleuze, et al., "Poly(p–acetoxystyrene) resin: a prospective new support for combinatorial synthesis", *J. Chem. Soc. Perkin Trans*, pp. 2217–2221 (1995).

*Primary Examiner*—Bernard Lipman
*Attorney, Agent, or Firm*—Matthew P. Vincent; Paula A. Campbell; Foley, Hoag & Eliot LLP

[57] ABSTRACT

The subject invention features substituted N-heteroaromatic compounds, libraries of substituted N-heteroaromatic compounds, and methods of synthesis thereof. For example, the present invention provides methods for synthesizing substituted N-heteroaromatic compounds, and is particularly amenable to the generation of libraries of substituted N-heteroaromatic compounds by combinatorial chemistry. The methods of the invention generally feature the reaction of O-linked heteroaromatic N-oxides with nucleophiles to produce substituted N-heteroaromatic compounds.

21 Claims, No Drawings

SYNTHESIS OF SUBSTITUTED N-HETEROAROMATIC COMPOUNDS AND METHODS OF USE THEREOF

BACKGROUND OF THE INVENTION

Substituted pyridines (and other N-heteroaromatic compounds) are widely distributed in nature, and many substituted synthetic N-heteroaromatic compounds are also important synthetic chemicals in the agrichemical and pharmaceutical industries. For example, certain substituted pyridines have herbicidal activity (see, e.g., U.S. Pat. Nos. 5,438,033 and 3,495,969); histamine antagonists (see, e.g., U.S. Pat. No. 5,432,175); fungicides (see, e.g., U.S. Pat. No. 5,185,339); and ferroelectric liquid crystals (see, e.g., U.S. Pat. No. 5,145,601); and as intermediates in synthesis. There are numerous references to the synthesis of substituted pyridine compounds; however, many of these reported approaches can be used to synthesize only a few types of substituted pyridine compounds.

SUMMARY OF THE INVENTION

The subject invention features substituted N-heteroaromatic compounds, libraries of substituted N-heteroaromatic compounds, and methods of synthesis thereof.

In one aspect, the invention provides a method for synthesizing a substituted N-heteroaromatic compound The method comprises reacting a heteroaromatic N-oxide with a functional group of a polymeric support to form a polymer-supported O-linked heteroaromatic N-oxide, and reacting a nucleophile with the polymer-supported O-linked heteroaromatic N-oxide to form a substituted N-heteroaromatic compound. In preferred embodiments, the polymeric support is insoluble. In other preferred embodiments, the polymeric support is soluble. In selected embodiments, the polymeric support comprises polyethylene glycol. In preferred embodiments, the functional group of a polymeric support is an acid halide, more preferably an acid chloride. In other preferred embodiments, the functional group of a polymeric support is a sulfonyl halide. In yet other embodiments, the functional group of a polymeric support is a phosphoryl halide. In still other embodiments, the functional group of a polymeric support is a benzyl halide. In preferred embodiments, the method includes the further step of purifying the O-linked heteroaromatic N-oxide.

In certain preferred embodiments, the heteroaromatic N-oxide is represented by the formula:

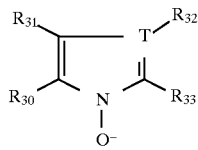

wherein

T is N (e.g., N⁺) or C;

$R_{30}$, $R_{31}$, $R_{32}$, and $R_{33}$ are independently selected from the group consisting of hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or $R_{30}$ and $R_{31}$ taken together form a carbocycle or heterocycle having from 4 to 10 atoms in the ring; with the proviso that if T is N, $R_{32}$ is alkyl, aralkyl, or aryl.

In other preferred embodiments, the heteroaromatic N-oxide is represented by the formula:

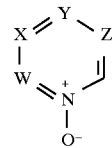

wherein

W, X, Y, and Z are each independently selected from the group consisting of N and $CR_1$, wherein each $R_1$ is independently selected from the group consisting of hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two $R_1$ taken together form a carbocycle or heterocycle having from 4 to 10 atoms in the ring structure.

In more preferred embodiments the heteroaromatic N-oxide is represented by the formula:

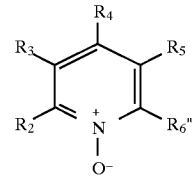

wherein $R_2$, $R_3$, $R_4$, $R_5$ and $R_{6''}$ each independently represent hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two of $R_2$, $R_3$, $R_4$, $R_5$ and $R_{6''}$ taken together form a carbocycle or heterocycle having from 4 to 10 atoms in the ring structure; with the proviso that at least one of $R_2$, $R_4$, and $R_6$ is hydrogen.

In still other preferred embodiments, the heteroaromatic N-oxide is represented by the formula:

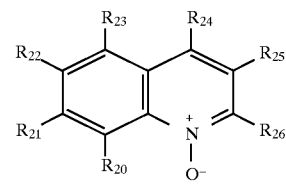

wherein $R_{20}$, $R_{21}$, $R_{22}$, $R_{23}$, $R_{24}$, $R_{25}$ and $R_{26}$ each independently represent hydrogen, halogen, alkyl, alkenyl, alkynyl, alkoxy, amino, carbonyl, cyano, thiol, thioalkoxy, aryl, amido, hydroxyl, carbamoyl, nitro, and trifluoromethyl, or any two of $R_{20}$, $R_{21}$, $R_{22}$, $R_{23}$, $R_{24}$, $R_{25}$ and $R_{26}$ taken together form a carbocycle or heterocycle having from 4 to 10 atoms in the ring structure; with the proviso that at least one of $R_{21}$, $R_{23}$, $R_{24}$ and $R_{26}$ is hydrogen.

In preferred embodiments, the nucleophile is represented by the formula:

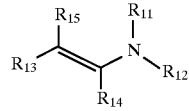

wherein $R_{11}$ and $R_{12}$ each independently represent alkyl, cycloalkyl, alkenyl, —$(CH_2)_m$—$R_7$, wherein $R_7$ represents aryl, cycloalkyl, cycloalkenyl, heterocyclyl or polycyclyl;

and m is zero or an integer in the range of 1 to 8; or $R_{11}$ and $R_{12}$ taken together with the N atom to which they are attached complete a heterocycle having 5 or 6 atoms in the ring structure; and $R_{13}$, $R_{14}$ and $R_{15}$ each independently represent hydrogen, alkyl, cycloalkyl, alkenyl, or —$(CH_2)_m$—$R_7$; or $R_{13}$ and $R_{14}$ taken together with the ethylidene moiety to which they are attached complete a ring having from 4 to 8 atoms in the ring structure; or $R_{11}$ and $R_{15}$, taken together with the N atom and ethylidene moiety to which they are respectively attached, complete a heterocycle having from 4 to 8 atoms in the ring structure.

In certain preferred embodiments the nucleophile is an indole. In other preferred embodiments, the nucleophile is an aromatic amine. In other preferred embodiments the nucleophile is selected from the group consisting of thiols, cyanide, amines, alkoxides, acetylides, hydroxide, and stabilized carbanions.

In another aspect, the invention features a method of synthesizing a compound represented by the formula:

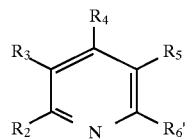

wherein $R_2$, $R_3$, $R_4$, and $R_5$ each independently represent hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two or more of $R_2$, $R_3$, $R_4$, and $R_5$ taken together form a carbocycle or heterocycle having from 4 to 10 atoms in the ring structure; and $R_{6'}$ is a nucleophile adduct; the method including:

a) reacting a heteroaromatic N-oxide represented by the formula:

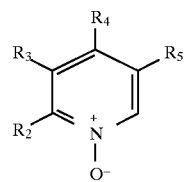

wherein $R_2$, $R_3$, $R_4$, and $R_5$ are as defined above; with a functional group of a polymeric support to form an O-linked heteroaromatic N-oxide; and b) reacting a nucleophile with said O-linked heteroaromatic N-oxide to form a substituted N-heteroaromatic compound.

In another aspect, the invention provides a method for synthesizing a library of substituted N-heteroaromatic compounds. The method comprises reacting a heteroaromatic N-oxide with a functional group of a polymeric support to form a polymer-supported O-linked heteroaromatic N-oxide, and reacting a nucleophile with the polymer-supported O-linked heteroaromatic N-oxide to form a library of substituted N-heteroaromatic compounds; wherein at least one of the heteroaromatic N-oxide and the nucleophile is provided as a variegated population.

In yet another aspect, the invention provides a method for synthesizing a library of substituted N-heteroaromatic compounds represented by the formula:

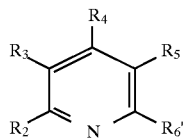

wherein $R_2$, $R_3$, $R_4$, $R_5$ and $R_6$ are as described above. The method comprises reacting a heteroaromatic N-oxide represented by the formula

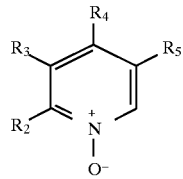

(wherein $R_2$, $R_3$, $R_4$, and $R_5$ are as defined above) with a functional group of a polymeric support to form an O-linked heteroaromatic N-oxide; and reacting a nucleophile with the of O-linked heteroaromatic N-oxide to form a library of substituted N-heteroaromatic compounds; wherein at least one of the heteroaromatic N-oxide and the nucleophile is provided as a variegated population.

In still another aspect, the invention features a library of substituted N-heteroaromatic compounds represented by the formula:

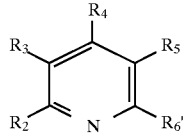

wherein $R_2$, $R_3$, $R_4$, $R_5$ and $R_{6'}$ are as described above. In preferred embodiments, $R_{6'}$ is represented by the formula:

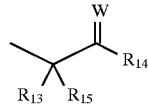

wherein
W is O or

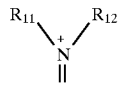

in which $R_{11}$ and $R_{12}$ each independently represent alkyl, cycloalkyl, alkenyl, —$(CH_2)_m$—$R_7$, wherein $R_7$ represents aryl, cycloalkyl, cycloalkenyl, heterocyclyl or polycyclyl; and m is zero or an integer in the range of 1 to 8; or $R_{11}$ and $R_{12}$ taken together with the N atom to which they are attached complete a heterocycle having 5 or 6 atoms in the ring structure; and $R_{13}$, $R_{14}$ and $R_{15}$ each independently represent hydrogen, alkyl, cycloalkyl, alkenyl, or —$(CH_2)_m$—$R_7$; or $R_{13}$ and $R_{14}$ taken together with the ethylene moiety to which they are attached complete a ring having from 4 to 8 atoms in the ring structure.

In preferred embodiments, the library comprises at least 100 different substituted N-heteroaromatic compounds.

In still another aspect, the invention provides a polymer-supported O-linked heteroaromatic N-oxide compound represented by the formula:

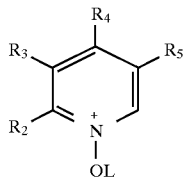

wherein $R_2$, $R_3$, $R_4$, and $R_5$ are as described above; and L is a polymeric support.

In another aspect, the invention provides a library of polymer-supported O-linked heteroaromatic N-oxide compounds represented by the formula:

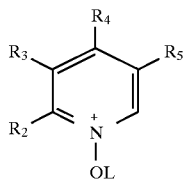

wherein $R_2$, $R_3$, $R_4$, and $R_5$ are as described above; and L is a polymeric support.

In still another aspect, the invention features a compound represented by the formula:

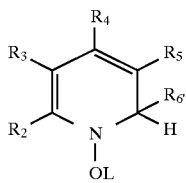

wherein $R_2$, $R_3$, $R_4$, $R_5$ and $R_{6'}$ are as described above; and L is a polymeric support.

In yet another aspect, the invention provides a library of compounds represented by the formula:

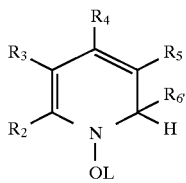

wherein $R_2$, $R_3$, $R_4$, and $R_5$ are as described above; and L is a polymeric support.

Still another aspect of the present invention concerns a method for identifying substituted N-heteroaromatic compounds which modulate the biological activity of a biological target, e.g., a protein, a nucleic acid, a lipid, or a combination thereof. In preferred embodiments, the assay includes contacting one or more subject N-heteroaromatic compounds with a biological target having a detectable biochemical activity. Such biological targets can be in the form of enzymes, receptors, subunits involved in formation of multimeric complexes, and the like, and having such biochemical activities as substrate conversion (catalysis of chemical reactions) or merely the ability to bind to a another molecule. The biological target can be provided in the form of a purified or semi-purified composition, a cell lysate, a whole cell or tissue, or even a whole organism. The level of biochemical activity is detected in the presence of the N-heteroaromatic compound, and a statistically significant change in the biochemical activity, relative to the level of biochemical activity in the absence of the compound, identifies the compound as a modulator, e.g., inhibitor or potentiator, of the biological activity of the target protein. In preferred embodiments, the N-heteroaromatic compound is provided as part of a compound library such as a combinatorial library, e.g., including detectable tags or which is amenable to deconvolution or which is provided in a spatially addressable format.

Likewise, certain of the N-heteroaromatic compounds generated by the subject method will be functional in non-biological uses such as material engineering. Similar to the assay set out above, the material of interest can be contacted with the subject N-heteroaromatic compound(s), or alternatively, formulated to include one or more of the subject N-heteroaromatic compounds. The effect of the compound on a particular characteristic of the material can be determined using routine techniques. For example, the ability of the compound to inhibit corrosion of a metal to which it is applied can be ascertained. In another embodiment, the non-linear optics can be determined for a liquid crystal display formulated with the compound. As above, preferred embodiments provide the material testing assay with N-heteroaromatic compounds in a library format.

DETAILED DESCRIPTION OF THE INVENTION

As described herein, the present invention provides methods for synthesizing substituted N-heteroaromatic compounds, and is particularly amenable to the generation of libraries of substituted N-heteroaromatic compounds by combinatorial chemistry. As described in more detail below, the methods of the invention generally feature the reaction of O-linked heteroaromatic N-oxides with nucleophiles to produce substituted N-heteroaromatic compounds.

Definitions

For convenience, certain terms employed in the specification, examples, and appended claims are collected here.

The term "heteroaromatic compound", as used herein, refers to an aromatic compound in which at least one atom of an aromatic ring is a heteroatom. The term "heteroatom", as used herein, refers to any atom that is not carbon or hydrogen. Preferred heteroatoms include O, S, N, P and the like. The term "N-heteroaromatic compound" refers to a heteroaromatic compound as described above wherein at least one heteroatom is nitrogen. Thus, an N-heteroaromatic compound can be represented by the formula:

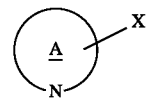

wherein A is an aromatic ring having from 5 to 7 atoms in the ring, and X is a substituent as described below. The ring A can, in general, be substituted with one or more substituents X, e.g., hydrogen, halogen, alkyl, alkenyl, alkynyl, alkoxy, amino, carbonyl, cyano, sulfhydryl, ureido, thioalkoxy, aralkyl, aryl, amido, hydroxyl, carbamoyl, nitro, and trifluoromethyl, and may be joined or fused to other rings, including aromatic or heteroaromatic rings. Exemplary N-heteroaromatic compounds include pyridine, pyridazine, pyrimidine, quinoline, acridine, imidazoles, benzimidazoles, and the like. A "substituted N-heteroaromatic compound" is an N-heteroaromatic compound in which at least one substituent is other than hydrogen.

The term "heteroaromatic N-oxide", as used herein, refers to an N-oxide of an N-heteroaromatic compound, as described above. Accordingly, a heteroaromatic N-oxide can be represented by the formula:

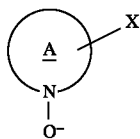

in which A is an aromatic ring and X is a substituent, as described above.

The term "O-linked heteroaromatic N-oxide", as used herein, refers to a heteroaromatic N-oxide in which an N-oxide oxygen atom is covalently bonded, in addition to being bonded to nitrogen, to an atom other than hydrogen. Exemplary O-linked heteroaromatic N-oxides include O-alkylated N-oxides and O-esterified N-oxides, where the ester may be organic or inorganic (e.g., acyl, sulfonyl, phosphoryl) and the like. When an O-linked heteroaromatic N-oxide is linked to a polymeric support by the O-linking moiety, a "polymer-supported O-linked heteroaromatic N-oxide" is formed.

The term "polymeric support", as used herein, refers to a soluble or insoluble polymer to which a heteroaromatic N-oxide can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if reaction of a heteroaromatic N-oxide with the polymeric support results in a soluble polymer-supported O-linked heteroaromatic N-oxide under the conditions employed. A polymeric support can be soluble under certain conditions and insoluble under other conditions. A polymeric support is termed "insoluble" if reaction of a heteroaromatic N-oxide with the polymeric support results in an insoluble polymer-supported O-linked heteroaromatic N-oxide under the conditions employed.

The term "functional group of a polymeric support", as used herein, refers to a chemical moiety of a polymeric support that can react with an N-oxide oxygen atom to form an O-linked heteroaromatic N-oxide. Thus, a functional group of a polymeric support must be sufficiently reactive to react with an N-oxide oxygen atom of a heteroaromatic N-oxide, and should not significantly react with other moieties present in the heteroaromatic N-oxide. Exemplary functional groups of a polymeric support include acid halides, acid anhydrides, N-sulfinyl sulfonamides (e.g., —SO$_2$NSO), sulfonylisocyanates, sulfonyl and phosphoryl halides, boron halides, and the like. Preferred functional groups of a polymeric support will form O-linked heteroaromatic N-oxides that are covalently bound to the polymeric support under mild conditions that do not adversely affect the polymer or the heteroaromatic N-oxide, and that are sufficiently stable to be isolated. Preferred functional groups of a polymeric support will also form O-linked heteroaromatic N-oxides in which the O-linked moiety comprises a good leaving group, as defined below.

The term "nucleophile" is recognized in the art, and as used herein means a chemical moiety having a reactive pair of electrons. Examples of nucleophiles include uncharged compounds such as amines, enamines, enols, mercaptans and alcohols, and charged moieties such as alkoxides, thiolates, carbanions, metallated amines (e.g., amine anions, for example, sodamide), and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, enolates, acetylides, Grignard reagents, organolithiums, and the like may, under approriate reaction conditions, be suitable nucleophiles.

The term "variegated population", as used herein, refers to a population including at least two different chemical entities, e.g., of different chemical structure. For example, a "variegated population" of heteroaromatic N-oxides would comprise at least two different heteroaromatic N-oxides. Similarly, a variegated population of nucleophiles comprises at least two different nucleophiles.

The term "nucleophile adduct", as used herein, refers to a covalently-bound substituent that results from addition of a nucleophile to a substrate according to the present invention. For example, addition of the cyanide nucleophile to a substrate yields a product in which the cyano substituent is a "nucleophile adduct".

The terms "electrophilic atom", "electrophilic center" and "reactive center" as used herein refer to the atom of the substrate that is attacked by, and forms a new bond to, the nucleophile.

The term "leaving group", as used herein, refers to a functionality that upon heterolytic bond cleavage departs with an electron pair.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl, alkoxyl, ester, ether, phosphoryl, amino, amido, imino, sulfhydryl, alkylthio, thioester, sulfonyl, nitro, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, iminos, amidos, phosphoryls (including phosphonates and phosphines), sulfonyls (including sulfates and sulfonates), and silyl groups, as well as ethers, alkylthios, selenoethers, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

As used herein, the term "nitro" means —$NO_2$; the term "halogen" designates —F, —Cl, —Br or —I; the term "sulfhydryl" means —SH; the term "hydroxyl" means —OH; the term "sulfonyl" means —$SO_2$—; and the term "organometallic" refers to a metal atom (such as mercury, zinc, lead, magnesium or lithium) or a metalloid (such as silicon, arsenic or selenium) that is bonded directly to a carbon atom, such as a diphenylmethylsilyl group.

The term "amino", as used herein, refers to a moiety that can be represented by the general formula:

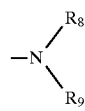

wherein $R_8$ and $R_9$ each independently represent a hydrogen, an alkyl, an alkenyl, —$(CH_2)_m$—$R_7$, —C(=O)—alkyl, —C(=O)—alkenyl, —C(=O)—alkynyl, —C(=O)—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocyclyl or a polycyclyl; and m is zero or an integer in the range of 1 to 8. Thus, the term "alkylamino" as used herein means an amino group, as defined above, having a substituted or unsubstituted alkyl attached thereto, i.e., at least one of $R_8$ and $R_9$ is an alkyl group.

The term "amido", as used herein, refers to a moiety that can be represented by the general formula:

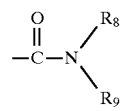

wherein $R_8$ and $R_9$ are as defined above.

The term "imino", as used herein, refers to a moiety that can be represented by the general formula:

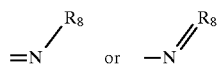

wherein $R_8$ is as described above.

The term "enamine", as used herein, refers to a moiety that can be represented by the general formula:

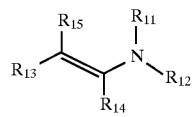

wherein $R_{11}$ and $R_{12}$ each independently represent an alkyl, a cycloalkyl, an alkenyl, —$(CH_2)_m$—$R_7$, wherein m and $R_7$ are as described above, or $R_{11}$ and $R_{12}$ taken together with the N atom to which they are attached complete a heterocycle having 5 or 6 atoms in the ring structure; and $R_{13}$, $R_{14}$ and $R_{15}$ each independently represent hydrogen, an alkyl, a cycloalkyl, an alkenyl, or —$(CH_2)_m$—$R_7$; or $R_{13}$ and $R_{14}$ taken together with the ethylidene moiety to which they are attached complete a ring having from 4 to 8 atoms in the ring structure; or $R_{11}$ and $R_{15}$, taken together with the N atom and ethylidene moiety to which they are respectively attached, complete a heterocycle having from 4 to 8 atoms in the ring structure.

The term "alkylthio" refers to an alkyl group, as defined above, having a sulfur radical attached thereto. In preferred embodiments, the "alkylthio" moiety is represented by one of —S—alkyl, —S—alkenyl, —S—alkynyl, and —S—$(CH_2)_m$—$R_7$, wherein m and $R_7$ are defined above. Representative alkylthio groups include methylthio, ethyl thio, and the like.

The term "carbonyl", as used herein, refers to a moiety that can be represented by the general formula:

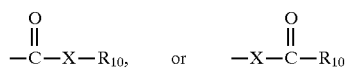

wherein X is a bond or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, and $R_{10}$ is not hydrogen, the formula represents an "ester". Where X is an oxygen, and $R_{10}$ is hydrogen, the formula represents a "carboxylic acid". Where X is a sulfur and $R_{10}$ is not hydrogen, the formula represents a "thioester." Where X is a bond, and $R_{10}$ is not hydrogen, the above formula represents a "ketone" group. Where X is a bond, and $R_{10}$ is hydrogen, the above formula represents an "aldehyde" group. Where the oxygen atom of the above formula is replaced by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O—alkyl, —O—alkenyl, —O—alkynyl, —O—$(CH_2)_m$—$R_7$, where m and $R_7$ are described above.

The term "phosphoryl", as used herein, refers to a moiety that can be represented by the general formula:

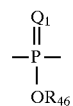

wherein $Q_1$ represents S or O, and $R_{46}$ represents hydrogen, a lower alkyl or an aryl. When used to substitute an alkyl, the phosphoryl group of the phosphorylalkyl can be represented by the general formula:

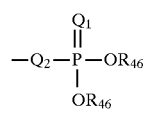

wherein $Q_1$ represented S or O, and each $R_{46}$ independently represents hydrogen, a lower alkyl or an aryl, $Q_2$ represents O, S or N.

The term "silyl", as used herein, refers to a moiety that can be represented by the general formula:

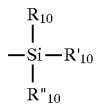

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, "alkylseleno" refers to an alkyl group having a seleno radical attached thereto. Exemplary "alkylselenos" that may be substituted on an alkyl are selected from one of —Se—alkyl, —Se—alkenyl, —Se—alkynyl, and —Se—$(CH2)_m$—$R_7$, m and $R_7$ being defined above.

The term "sulfonate", as used herein, refers to a moiety that can be represented by the general formula:

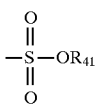

in which $R_{41}$ is an electron pair, hydrogen, alkyl or aryl.

The term "sulfate", as used herein, refers to a moiety that can be represented by the general formula:

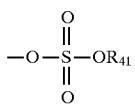

in which $R_{41}$ is as defined above; or $R_{41}$, taken together with the sulfonyl group and the oxygen atoms to which they are attached, may form a ring structure having from 5 to 10 members.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls, alkenoxyls, and alkynoxyls.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, selenoether, ketone, aldehyde, ester, a heterocyclyl, an aromatic or heteroaromatic moiety, —$CF_3$, —CN, or the like.

The terms "heterocyclyl" or "heterocyclic group" refer to 4- to 10-membered ring structures, more preferably 5- to 7-membered rings, which ring structures include one to four heteroatoms. Heterocyclyl groups include pyrrolidine, oxolane, thiolane, imidazole, oxazole, piperidine, piperazine, morpholine, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, selenoether, ketone, aldehyde, ester, a heterocyclyl, an aromatic or heteroaromatic moiety, —$CF_3$, —CN, or the like.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, selenoether, ketone, aldehyde, ester, a heterocyclyl, an aromatic or heteroaromatic moiety, —$CF_3$, —CN, or the like.

A "bridging substituent" refers to a substitution at two (or more) sites on a ring by the same (as opposed to identical) substituent so as to form a covalent bridge between the substitution sites. For example, a bridging substituent may be represented by the general formula or —$R_{16}$—$R_{17}$—$R_{18}$—, wherein $R_{16}$ and $R_{18}$ each independently are a bond or represent an alkyl, an alkenyl, or an alkynyl, preferably $C_1$ to $C_{10}$, and $R_{17}$ is a bond, amino, amido, phosphoryl, carbonyl, silyl, oxygen, a sulfonyl, sulfur, selenium, or an ester.

The term "carbocycle", as used herein, refers to an aromatic or non-aromatic ring in which each atom of the ring is carbon.

It will be understood by the skilled artisan that "substitution" or "substituted with" means that such substitution is in accordance with permitted valence of the substituted atom and the substituent. It will aslo be understood that substrates suitable for use in the invention, and substituted N-heteroaromatic compounds produced by the methods of the invention, are, in preferred embodiments, stable compounds which do not, in general, spontaneously undergo undesired transformation such rearrangement, cyclization, decomposition, etc.

Reactions

In one aspect, the present invention features a method for synthesizing substituted N-heteroaromatic compounds. One salient feature of the subject method is that immobilized intermediate compounds can be purified, if desired, to remove excess reagents and impurities. Thus, higher yields and purer products can be obtained by the present method. Another feature of the subject method is the amenability of the polymer-based chemistries to state-of-the-art combinatorial approaches that may require, for example, encoded tags, spatial addressability, or the like.

In general, the method features reacting a heteroaromatic N-oxide with a functional group of a polymeric support to form a polymer-supported O-linked heteroaromatic N-oxide, and then reacting a nucleophile with the polymer-supported O-linked heteroaromatic N-oxide to form a substituted N-heteroaromatic compound. Selection of nucleophile is based on the desired end product, and also on a need for a nucleophile to be reactive with the O-linked heteroaromatic N-oxide through nucleophilic attack at an atom of the heteroaromatic N-oxide, yet relatively unreactive to the O-linked moiety. Further guidance in selection of nucleophile is provided in more detail below. Conditions are maintained to first allow reaction of the nucleophile with the heteroaromatic N-oxide substrate, and then to allow the adduct to undergo cleavage of the N—O bond and thus form a substituted N-heteroaromatic compound. The nucleophile, substrate, and reaction conditions can be selected by those skilled in the art to provide reaction in a desired regiochemical sense.

In an exemplary reaction scheme, and without wishing to be bound by any theory, the reaction of a nucleophile with a polymer-supported O-linked heteroaromatic N-oxide can occur as illustrated below:

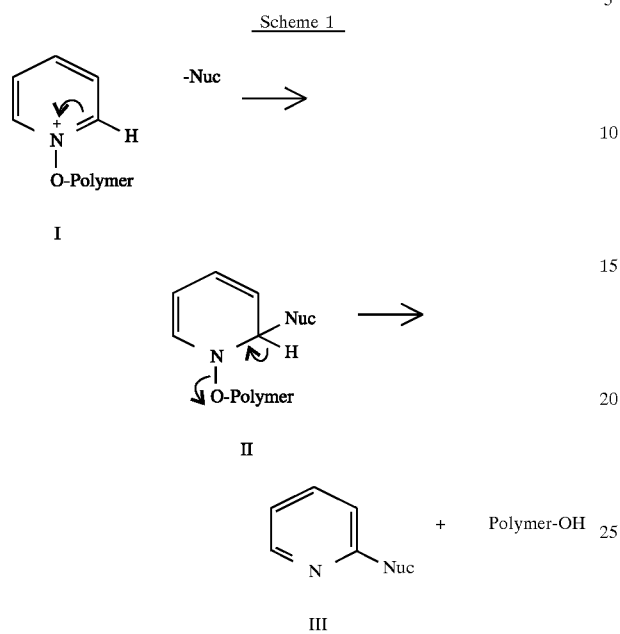

In Scheme 1, the nucleophile (which may be charged or uncharged and is denoted "⁻Nuc") reacts with the polymer-supported O-linked heteroaromatic N-oxide I to form an intermediate II. Elimination of the leaving group (and loss of a proton) results in rearomatization of the heterocyclic ring and formation of a substituted N-heteroaromatic compound III, along with the spent polymeric support ("Polymer—OH").

In another exemplary reaction scheme, and without wishing to be bound by any theory, the reaction of a nucleophile with a polymer-supported O-linked heteroaromatic N-oxide can occur as illustrated below:

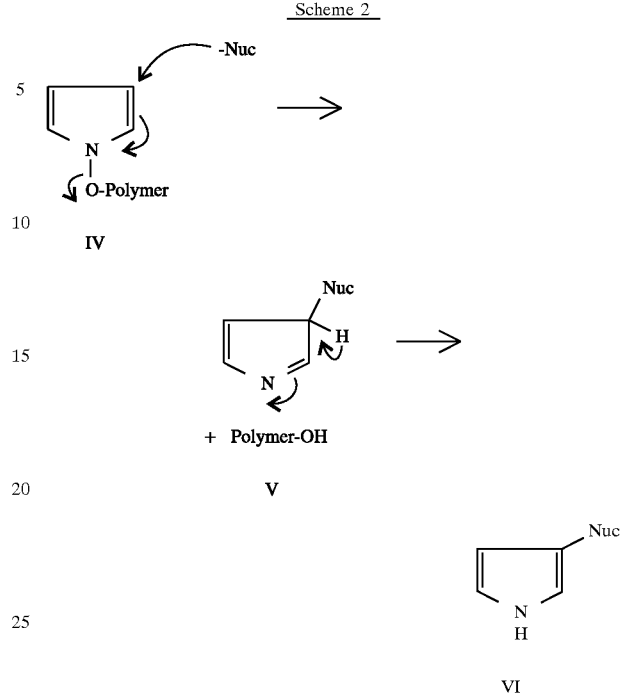

In Scheme 2, the nucleophile (which may be charged or uncharged and is denoted "⁻Nuc") reacts with the polymer-supported O-linked heteroaromatic N-oxide IV to expel the leaving group and form an intermediate V. Rearrangement results in rearomatization of the heterocyclic ring and formation of a substituted N-heteroaromatic compound VI, along with the spent polymeric support ("Polymer—OH").

Thus, in an exemplary embodiment, the invention features a method of synthesizing a 6-substituted pyridine, as illustrated below:

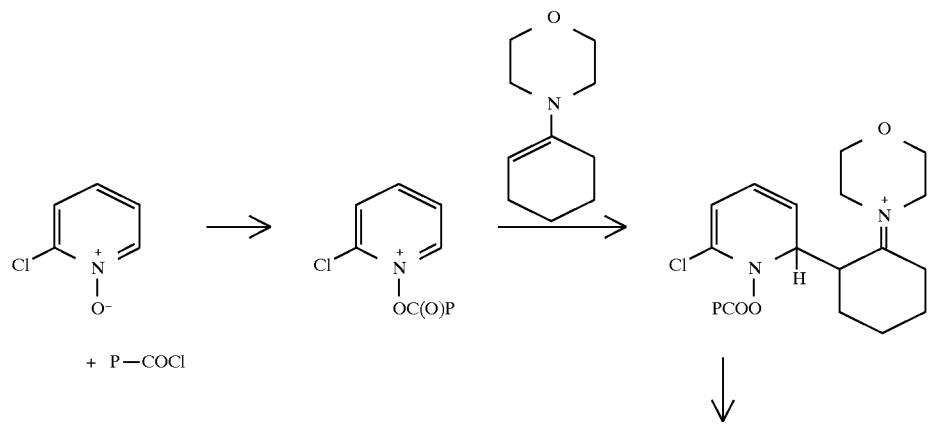

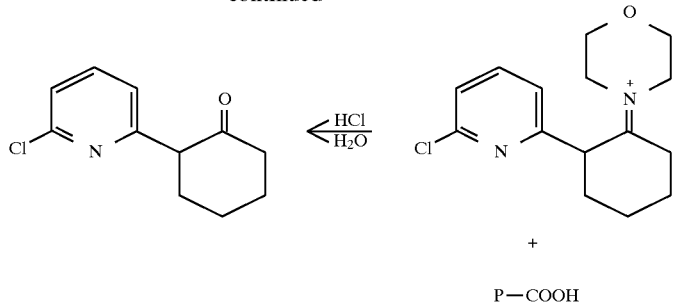

wherein P—COCl represents a polymer-supported carboxylic acid chloride. Hydrolysis of the imine adduct yields 2-(6-chloro-2-pyridyl)cyclohexanone.

In another illustrative embodiment, the invention features a method of synthesizing 4-substituted pyridines according to the scheme:

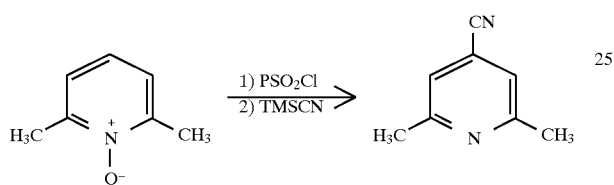

wherein PSO$_2$Cl represents a polymer-supported sulfonyl chloride and TMSCN is trimethylsilylcyanide.

In yet another illustrative embodiment, the invention provides a method of synthesizing a substituted quinoline compound according to the scheme:

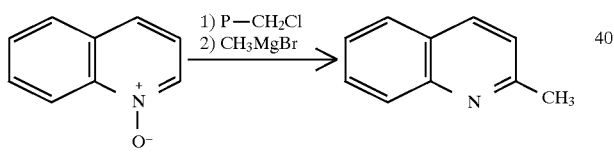

in which P—CH$_2$Cl represents a chlorinated polymer. The product, quinaldine, is useful as an anaesthetic in fish.

In still another exemplary embodiment, the invention features a method of synthesizing substituted benzimidazole compounds according to the scheme:

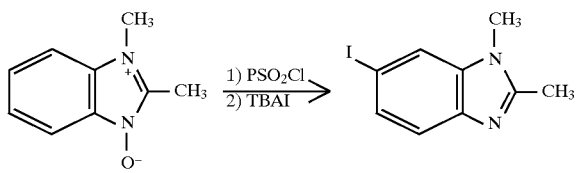

in which PSO$_2$Cl represents a polymer-supported sulfonyl chloride and TBAI is tetrabutylammonium iodide.

In yet another exemplary embodiment, the invention features a method of synthesizing substituted indole compounds according to the scheme:

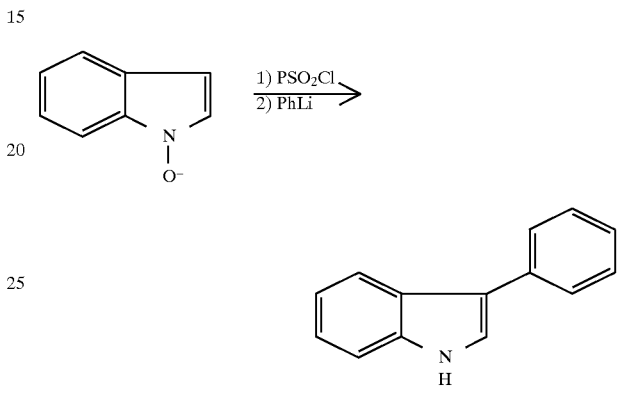

in which PSO$_2$Cl represents a polymer-supported sulfonyl chloride and PhLi is phenyllithium.

In another illustrative embodiment, the invention provides a method of synthesizing substituted pyrrole compounds according to the scheme:

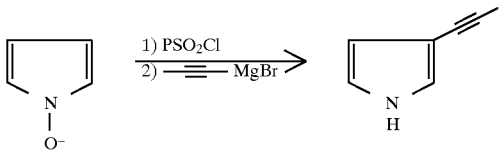

in which PSO$_2$Cl represents a polymer-supported sulfonyl chloride and the nucleophile is propynylmagnesium bromide.

The substituted N-heteroaromatic products produced by the synthetic processes of this invention can be purified by conventional means, including, for example, distillation, chromatography, crystallization, and the like. The substituted N-heteroaromatic products produced by the synthetic processes of this invention can also undergo further reaction(s) to afford desired derivatives thereof. Such derivatization reactions can be carried out in accordance with conventional procedures known in the art. For example, suitable derivatization reactions include esterification, oxidation of alcohols to aldehydes or ketones, hydrolysis of imines, N-alkylation of amines, reduction of ketones, α-alkylation of ketones by alkyl halides, acylation of amines and the like. To further illustrate, exemplary classes of pharmaceuticals that can be synthesized by a scheme including the subject reactions are cardiovascular drugs, nonsteroidal antiinflammatory drugs, central nervous system agents, and antihistamines.

Substrates

Substrates useful in the methods of the present invention are N-oxides of N-heteroaromatic compounds. In general, the N-oxides will themselves be aromatic, and are referred to herein as heteroaromatic N-oxides. Substrates are selected based on the structure of the desired product, the reactivity of a particular substrate with a selected nucleophile, and the like. The selection of an appropriate substrate will be routine to one of skill in the art.

The substrate preferably will not contain any interfering functionalities. In general, an appropriate substrate will contain a reactive electrophilic center where a nucleophile may attack, eventually resulting in cleavage of an N—O bond, after formation of a covalent bond between the nucleophile and the substrate, to yield a substituted N-heteroaromatic compound. It will also be understood that not all substrates will react with all nucleophiles. The reactions of heteroaromatic N-oxides with nucleophiles are described in, e.g., A. R. Katritzky and J. M. Lagowski, "Chemistry of the Heterocyclic N-Oxides", Chapter 3, Academic Press, New York, N.Y., (1971), and references cited therein.

Examples of substrates suitable for use in the methods of the present invention include N-oxides of pyridines, quinolines, isoquinolines, acridines, pyrazines, quinazolines, pyridazines, cinnolines, pyrimidines, triazines, pyrindines, naphthyridines, and the like. Other substrates suitable for use in the methods of the invention include pyrroles, imidazoles, indoles, benzimidazoles and the like.

Heteroaromatic N-oxide substrates suitable for use in the methods of the invention can be purchased from commercial sources or can be synthesized according to methods known in the art. For example, heteroaromatic N-oxides can be synthesized from the corresponding N-heteroaromatic compound by oxidation, e.g., with a peracid such as peracetic acid or m-chloroperoxybenzoic acid. The preparation of heteroaromatic N-oxides is further described in, e.g., A. R. Katritzky and J. M. Lagowski, "Chemistry of the Heterocyclic N-Oxides", op. cit., Chapter 2. Many N-heteroaromatic compounds are available from commercial sources (e.g., over 100 substituted pyridines are available from Aldrich Chemical, Milwaukee, Wis.).

In general, a substrate is selected to undergo reaction with a nucleophile in a desired regiochemical sense, e.g., at a desired electrophilic center of the substrate. In substrates with more than one electrophilic center, the nucleophile, polymeric support, and reaction conditions can be selected to insure reaction at the desired site. Furthermore, the substrate can include functionalities that promote reaction with a nucleophile at a particular site. Exemplary functionalities that can influence the regiochemical site of nucleophilic attack include groups that sterically hinder approach to an undesired electrophilic center (e.g., a bulky substituent such as t-butyl); electron-withdrawing or electron-donating groups that can electronically direct an attacking nucleophile to, or away from, a selected site; or blocking groups that prevent reaction at an undesired site. In preferred embodiments, a blocking group can be selectively removed at a later stage of the synthesis. For example, a chlorine atom positioned to block nucleophilic attack at an aromatic substrate electrophilic center can be removed by, e.g., hydrogenation, to yield a desired dechlorinated compound. The selection of functionalities that influence the regiochemical sense of nucleophile attack will be routine to the skilled artisan.

Nucleophiles

Suitable nucleophiles may be selected by the skilled artisan according to several criteria. In general, a suitable nucleophile will have one or more of the following properties: 1) It will be capable of reacting with the substrate at the desired electrophilic site; 2) It will yield a useful product upon reacting with the substrate; 3) It should not substantially react with the substrate at functionalities other than the desired electrophilic site; 4) It will not substantially undergo further undesired reaction after reacting with the substrate in the desired sense. While undesirable side reactions (such as reactions with the support) may occur, the rates of such reactions can be manipulated through the selection of reactants and conditions to be slow in comparison with the rate of the desired reaction(s).

Nucleophiles that satisfy the above criteria can be chosen for each substrate and will vary according to the substrate structure and the desired product. Routine experimentation may be necessary to determine the preferred nucleophile for a given transformation. For example, different enamines (of a selected ketone or aldehyde) may have differing reactivities, and thus routine experimentation may be required to determine the optimal enamine nucleophile. Other "enamine-like" nucleophiles include aromatic amines, indoles, pyrroles, and antipyrines. In a preferred embodiment, the nucleophile is an enamine.

In addition to enamines, other nucleophiles that can react with a substrate to form a bond to a nucleophile carbon atom include carbon nucleophiles such as enols, enol silyl ethers, metallated enamines, indole or pyrrole anions, cyanide, acetylides, 1,3-dithiane anion, or stabilized carbon nucleophiles such as enolates (illustratively of active hydrogen compounds such as malonic esters or 1,3-diketones), alkyl nitro compounds and the like.

Nucleophiles that can react with a substrate to form a bond to a nucleophile nitrogen atom include azide, phthalimide, amines, amine anions (for example, sodamide or lithiated amines) and N-heteroaromatic compounds such as pyridine.

Nucleophiles that can react with a substrate to form a bond to a nucleophile sulfur atom include mercaptans, thiolates, bisulfite, thiocyanate and the like.

In certain embodiments, halogens can be used as nucleophiles. Reagents such as metal and tetraalkylammonium salts of halogens such as Cl, Br, and I can be used to provide a halogen atom to a product according to the present invention.

For any of the above nucleophiles that exist as anions, the counterion can be any of a variety of conventional cations, including, but not limited to, alkali and alkaline earth metal cations. Preferred cations include lithium,sodium, potassium, and magnesium. In some cases, nonionic reagents may be useful; for example trimethylsilyl azide (TMS-N$_3$) can be used to deliver the azide nucleophile, and trimethylsilyl cyanide (TMS—CN) can be used to deliver the cyanide nucleophile.

Organometallic reagents such as simple or higher-order organocuprate or organozinc species may also be useful. In certain embodiments, Grignard reagents or organolithium reagents may be employed as nucleophiles.

Supports

The methods of the invention include the use of a polymeric support that includes a functional group capable of reacting with an N-oxide oxygen of a heteroaromatic N-oxide to form an O-linked heteroaromatic N-oxide.

The choice of a suitable polymeric support functional group will be routine to the skilled artisan. In general, the polymeric support functional group will be selected according to at least some of the following criteria: it should 1) be reactive under conditions that will not generally cause substantial undesired degradation of the support or the substrate; 2) result in formation of an O-link that is a good leaving group. In preferred embodiments, reaction of the polymeric support functional group with a heteroaromatic N-oxide will result in the formation of an isolatable or purifiable O-linked heteroaromatic N-oxide. In preferred embodiments, the polymeric support has a functional group capacity of at least 0.5 mmol/g.

A polymeric support functional group should be selected to activate the substrate such that the desired reaction takes place at a selected electrophilic center with a particular nucleophile. Accordingly, the choice of polymeric support functional group will be determined, at least in part, by the particular substrate and nucleophile employed. For example, a polymeric support with sulfonyl halide functional groups is believed in general to provide substrates with access to a broader variety of nucleophiles than will be available for use when a carboxylic acid halide functional group is employed. This is due, at least in part, to the facts that 1) the linking sulfur-oxygen bond is resistant to nucleophilic attack and 2) sulfonates are, in general, better leaving groups than carboxylates.

Suitable polymeric support functional groups include halides, anhydrides, and active esters (e.g., carboxylate esterified with a good leaving group) of carboxylic acids; sulfonyl halides; phosphoryl halides; boron halides; N-sulfinyl sulfonamides; sulfonylisocyanates; and the like. In a preferred embodiment, the polymeric support functional group is a carboxylic acid halide, more preferably an acid chloride. In another preferred embodiment, the polymeric support functional group is a sulfonic acid halide, more preferably a sulfonyl chloride.

Other suitable polymeric support functional groups include alkyl halides (such as benzyl halides or sulfonates) and other reactive functional groups that can react in an $S_N2$ mode with the N-oxide oxygen atom of a heteroaromatic N-oxide. Supports that, when reacted with a heteroaromatic N-oxide, result in an O-alkyl or O-aralkyl link, are particularly useful when it is desired to employ nucleophiles such as Grignard reagents and organolithium reagents.

A leaving group is a functionality that upon bond cleavage departs with an electron pair. A good leaving group is a leaving group that departs easily, generally under relatively mild conditions. In general, good leaving groups are those moieties that are expelled from the substrate as weak bases. For example, sulfates, sulfonates, phosphates and the like are good leaving groups. In addition, some moieties may be good leaving groups when protonated or complexed with a Lewis acid. For example, alkoxide ions are generally modest leaving groups, but alcohols are better leaving groups. In general, for use in the subject methods, the leaving group should be good enough to allow elimination of the leaving group moiety (e.g., the O-link functionality including the polymeric support) under conditions that do not adversely affect the formation of the desired product.

Polymeric supports with appropriate functional groups are known in the art and can be prepared by known techniques. For example, polymers including the carboxylic acid chloride functionality (e.g., —COCl) are known (see, e.g., P. Hodge and D. C. Sherrington, "Polymer-supported Reactions in Organic Synthesis", Chapter 1, (1980)) and can be prepared by treatment of conventional polymer-supported carboxylic acids (e.g., polyacrylic acids) with, e.g., thionyl chloride, oxalyl chloride, and the like. Polymeric supports including sulfonyl chloride functionalites can be obtained by the reaction of a polymer including sulfonic acid moieties (e.g., —SO$_3$H) with, e.g., thionyl chloride, or by other known methods, for example, the method described in U.S. Pat. No. 5,118,766. Benzyl halide-containing polymers are well known and include chloromethylated polystyrene (e.g., Merrifield resin).

For ease of use and lower cost, it is desirable that the polymeric support be easily recyclable. Thus, a polymeric support including —COCl functionalities becomes, after a reaction according to the subject invention, a spent polymeric support with —COOH functionalities. Treatment of the spent polymeric support as described supra (e.g., with thionyl chloride) regenerates the polymer support with -COCl functionalities. Thus, in a preferred embodiment, the polymeric support can be regenerated.

Soluble polymeric supports include functionalized polymers based on polyvinyl alcohol or polyethylene glycol (PEG). A soluble support can be made insoluble (e.g., can be made to precipitate) by addition of a suitable inert nonsolvent. One advantage of reactions performed using soluble polymeric supports according to the invention is that reactions in solution can be more rapid, higher yielding, and/or more complete than reactions that are performed on insoluble polymeric supports.

Insoluble polymeric supports include functionalized polymers based on polystyrene, polystyrene/divinylbenzene copolymers, and other polymers known to the skilled artisan.

Reaction conditions

The reactions of the present invention may be performed under a wide range of conditions, though it will be understood that the solvents and temperature ranges recited herein are not limitative and only correspond to a preferred mode of the process of the invention.

In general, it is desirable that reactions are run using mild conditions that will not adversely affect the substrate, the nucleophile, the intermediates, or the product. For example, the reaction temperature influences the speed of the reaction, as well as the stability of the reactants and catalyst. The reactions will usually be run at temperatures in the range of −78° C. to 100° C., more preferably in the range −20° C. to 50° C. and still more preferably in the range −20° C. to 25° C.

In general, the reactions according to the invention will be performed in the liquid phase, e.g., in solution or suspension. The reactions may be run in an inert solvent, preferably one in which the reaction ingredients, optionally including the polymeric support, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent that is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred.

In certain embodiments it is preferable to perform the reactions under an inert atmosphere of a gas such as nitrogen or argon.

In preferred embodiments, the reaction conditions are selected to permit isolation or purification of the polymer-supported O-linked heteroaromatic N-oxide (i.e., bound to the polymeric support, e.g., structure I in Scheme 1)). For example, a soluble polymeric support conjugated to a heteroaromatic N-oxide as described above can be precipitated by the addition of an inert nonsolvent, and the precipitate washed with an inert nonsolvent to remove, or reduce the amount of, impurites and unreacted materials. In another illustrative embodiment, an insoluble polymeric support conjugated to a heteroaromatic N-oxide can be separated from a reaction mixture by, e.g., filtration, and washed to remove, or reduce the amount of, impurities and unreacted materials. The purified polymeric-support-bound heteroaromatic N-oxide can then be reacted with a nucleophile(s) to yield the desired product(s).

In more preferred embodiments, the reaction conditions are selected to permit isolation or purification of the adduct resulting from the addition of a nucleophile to the polymer-supported O-linked heteroaromatic N-oxide (e.g., structure II in Scheme 1) before rearomatization occurs. By purifying the adduct II at this stage, the unreacted starting materials and other contaminants can be easily removed (as described above for the polymer-supported O-linked heteroaromatic N-oxide), or reduced in amount, before the substituted N-heteroaromatic compound is released into solution.

Libraries

In another aspect, the invention features libraries of substituted N-heteroaromatic compounds, libraries of O-linked heteroaromatic N-oxides, and methods of synthesizing libraries of substituted N-heteroaromatic compounds.

The synthesis of combinatorial libraries is well known in the art and has been reviewed (see, e.g., E. M. Gordon et al., *J Med. Chem.* 37:1385–1401 (1994)). The subject invention contemplates methods for synthesis of combinatorial libraries of substituted N-heteroaromatic compounds and of O-linked heteroaromatic N-oxides. Such libraries can be synthesized according to a variety of methods. For example, a "split-pool" strategy can be implemented in the following way: beads of a functionalized polymeric support are placed in a plurality of reaction vessels. To each aliquot of beads is added a solution of a different heteroaromatic N-oxide, and the reactions proceed to yield a plurality of O-linked heteroaromatic N-oxides. The aliquots of derivatized beads are then washed, "pooled" (i.e., recombined), and the pool of beads is again divided, with each aliquot being placed in a separate reaction vessel. To each reaction vessel is added a solution of a different nucleophile, and reaction occurs to yield a plurality of reaction vessels each containing a plurality of substituted N-heteroaromatic compounds.

In another illustrative synthesis, a "diversomer library" is created by the method of Hobbs DeWitt et al. (*Proc. Natl. Acad. Sci. U.S.A.* 90:6909 (1993)). Aliquots of functionalized polymeric support beads are placed in an array of reaction vessels, and one of a plurality of heteroaromatic N-oxides is introduced into each vessel. After reaction, the beads are washed to yield an array of polymer-supported O-linked heteroaromatic N-oxides. Each vessel in the array is then reacted with one of a plurality of nucleophiles. After reaction, purification and workup yields a soluble library of substituted N-heteroaromatic compounds.

Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem., op. cit.*). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

Combinatorial libraries of compounds can also be synthesized with "tags" to encode the identity of each member of the library (see, e.g., W. C. Still et al., PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of N-heteroaromatic compounds of the invention contain at least 30 compounds, more preferably at least 100 compounds, and still more preferably at least 500 compounds. In preferred embodiments, the libraries of N-heteroaromatic compounds of the invention contain fewer than $10^9$ compounds, more preferably fewer than $10^8$ compounds, and still more preferably fewer than $10^7$ compounds.

Assays

Another aspect of the present invention provides the subject substituted N-heteroaromatic compounds in assays designed for detecting distinct activities of a molecule, e.g., of either a biological or non-biological nature. In particular, the present invention specifically contemplates the screening of substituted N-heteroaromatic compounds, especially libraries of these compounds, in assays designed to detect potential therapeutic agents, anti-fungal agents, insecticides and/or agricultural agents such as herbicide and other defoliants. In illustrative embodiments, compounds synthesized by the subject method can be tested for such activities as, for example, substituted N-heteroaromatics are presently used in the art, such as: inhibition of thromboxane A2 synthase, e.g., for use in treating ischemic heart diseases, thromboembolic disorders, cerebral circulatory disorders and/or asthma; antagonism of angiotensin II receptors, e.g., for use as a vasodilator in, for example, the treatment of congestive heart failure, hypertension and/or renal dysfunctions; inhibition of prolyl 4-hydroxylase, e.g., for use in treatment of disorders in which the storage of collagens contributes decisively to the symptoms, e.g., for reducing collagen synthesis and fibrosis in patients with systemic sclerosis; inhibition of HMG-CoA reductase, e.g., for control of cholesterol levels; antagonism of leukotriene binding to neutrophils, or antagonism of histamine receptors, e.g., for treatment of inflammatory and allergic diseases and disorders, as well as treatment of gastrointestinal hyperacidity and ulcerogenic disorders.

Furthermore, the present invention also contemplates assays which ascertain the usefulness of an N-heteroaromatic compound, as may synthesized by the subject method, in non-biological uses, such as material engineering processes. For example, the subject substituted N-heteroaromatic compounds can be used in the generation of nonlinear optical complexes for liquid crystal displays, or in the formulation of corrosion inhibitors for metals.

A variety of assay formats will suffice and, in light of the present disclosure, those not expressly described herein will nevertheless be comprehended by one of ordinary skill in the art. Substituted N-heteroaromatic compounds to be tested for a particular activity can be individually synthesized by the subject method, though in preferred embodiments, the compounds will be generated as combinatorial libraries as described above and generally known in the art.

Exemplified below are drug screening assays utilizing substituted N-heteroaromatic compounds such as generated by the subject method. These are meant merely for illustrative purposes. The choice of target, e.g., prolyl 4-hydroxylase or histamine receptor, is merely for convience and clarity.

In many drug screening programs which test libraries of compounds, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an inhibition of enzymatic activity.

Where the target is an enzymatic activity, such as prolyl 4-hydroxylase, the preferred screening assays will be generated to detect inhibition of substrate conversion to product. Accordingly, in an exemplary screening assay of the present invention, the substituted N-heteroaromatic compound(s) are contacted with a reaction mixture including prolyl 4-hydroxylase which is ordinarily capable of hydroxylating a proline containing peptide substrate, and a substrate for the enzyme, e.g., collagen or a peptide substrate as described in Atreya et al. (1991) *J Biol. Chem.* 266:2852. Detection of the rate of product formation provides a means for determining the compound's efficacy at inhibiting the activity of prolyl 4-hydroxylase. The efficacy of the compound can be assessed by generating dose response curves from data obtained using various concentrations of the test compound.

In an exemplary embodiment, the following procedure known in the art is used to test the substituted N-heteroaromatic compounds in vitro for prolyl-4-hydroxylase inhibition. Purified mammalian prolyl-4-hydroxylase (EC 1.14.11.2:prolyl-glycyl-peptide, 2-oxyglutarate: oxidoreductase) is incubated with substrates (i.e., native unhydroxylated collagen of either 60,000 molecular weight, $K_m 10^{-8}M$; or 90,000 molecular weight, $K_m 10-11M$), α-ketoglutarate, oxygen, and enzyme cofactors, with or without the test compounds. Enzymatic activitiy is determined by measuring release of tritiated water during the hydroxylation of $^3$H-peptidyl proline or release of $^{14}CO_2$ formed from the coupled decarboxylation of $^{14}$C-α-ketoglutarate.

In other embodiments, inhibitory activity is assayed by the method of R. E. Rhoads (1971) *Methods in Enzymology* XVIIB, 306, using a partially purified enzyme preparation derived from chick embryo in accordance with the methods of K. I. Kivirriko et al. (1967) *J Biol. Chem.* 242:4007 and J. Halme et al (167) *Biochimica et Biophysica Acta* 198:460 and, as the substrate, (Pro-Pro-Gly)$_5$, 4H$_2$O [manufactured by Tanpakushitsu Kenkyu Shoreikai (Protein Research Foundation Society), Osaka, Japan].

In still other embodiments, such as receptor antagonism, the assay can be formulated to detect the ability of a test compound to inhibit binding, competitive and non-competitive, of a ligand to a target receptor. The inhibition of complex formation between, to illsutrate, the histamine H2-receptor and a known ligand may be detected by a variety of techniques. For instance, modulation of the formation of complexes can be quantitated using, for example, detectably labelled ligands such as radiolabelled (e.g. $^{32}$P, $^{35}$S, $^{14}$C or 3H), fluorescently labelled (e.g. FITC), or enzymatically labelled ligands, by immunoassay, or by chromatographic detection.

To illustrate, there are a variety of binding assays known in the art for detecting H2-receptor antagonists based on their ability to inhibit binding of known H2 receptor ligands (including other antagonists). In one embodiment, the in vitro assay described by Norris et al. (1985) *Agents Actions* 16:170 can be used to score for substituted N-heteroaromatics which bind to the H2-receptor (and which may be further characterized in subsequent biological assays as agonists or antagonists of that receptor). In particular, the Norris et al. assay utilizes a competitive binding assay which detects inhibition of $^3$H-tiotidine binding to guinea-pig cerebral cortex H2 receptors.

In certain assays, the receptor, subunits thereof, or even other target protein to which binding is to be assessed, can be provided in a pure or semi-pure form. Typically, for those instances, it will be desirable to immobilize one of either the receptor or ligand to facilitate separation of receptor/ligand complexes from uncomplexed forms, as well as to accommodate automation of the assay. Binding of the ligand to the receptor, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the receptor or ligand to be bound to a matrix. For example, glutathione-S-transferase(GST)/receptor fusion proteins can be adsorbed onto glutathione sepharose beads (Sigma Chemical, St. Louis, Mo.) or glutathione derivatized microtitre plates, which are then combined with the ligand, e.g. a labeled ligand, and the test compound, and the mixture incubated under conditions conducive to complex formation. Following incubation, the beads are washed to remove any unbound ligand, and the matrix immobilized label determined directly, or in the supernatant after the receptor/ligand complexes are subsequently dissociated. When amenable, the complexes can be dissociated from the matrix, separated by SDS-PAGE, and the level of ligand found in the bead fraction quantitated from the gel using standard electrophoretic techniques.

Other techniques for immobilizing proteins on matrices are also available for use in the subject assay. For instance, either of the receptor or ligand proteins can be immobilized utilizing conjugation of biotin and streptavidin. For instance, biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the receptor but which do not interfere with ligand binding can be derivatized to the wells of the plate, and the receptor trapped in the wells by antibody conjugation. As above, preparations of a ligand and a test compound are incubated in the receptor-presenting wells of the plate, and the amount of receptor/ligand complex trapped in the well can be quantitated. Exemplary methods for detecting such complexes, in addition to those described above, include immunodetection of complexes using antibodies reactive with the ligand, or which are reactive with the receptor protein and compete for binding with the ligand.

Exemplification

EXAMPLE 1

To a stirred suspension of polyacrylic acid (available from Aldrich) in methylene chloride maintained at a temperature of −20° to 0° C. is slowly added a 10-fold molar excess of thionyl chloride by syringe under an inert atmosphere of argon. After 30 minutes, the solvents are removed by filtration and the acid chloride resin washed with methylene chloride until all HCl is removed. The resin is suspended in tetrahydrofuran (THF) and a 5-fold excess of a 2-chloropyridine-N-oxide is added. After allowing the reaction to go to completion, the insoluble O-linked chloropyridine N-oxide ester is collected and washed thoroughly with THF and then allowed to react with a 5-fold excess of the morpholine enamine of cyclohexanone in chloroform with stirring under an inert atmosphere of argon for 8 hours at room temperature. Aqueous HCl (1N) is added and the mixture stirred until hydrolysis is complete. The mixture is made basic by the addition of potassium carbonate the aqueous phase is filtered and extracted with chloroform. The chloroform extracts are evaporated and the residue purified by flash chromatography to yield 2-(6-chloro-2-pyridyl) cyclohexanone.

Those skilled in the art will recognize, or be able to ascertain using no more than routine experimentation, numerous equivalents to the specific procedures described herein. Such equivalents are considered to be within the scope of this invention and are covered by the following claims.

The contents of all references described herein are hereby incorporated by reference.

Other embodiments are within the following claims.

What is claimed is:

1. A method for synthesizing a substituted N-heteroaromatic compound, the method comprising:
   a) reacting a heteroaromatic N-oxide in a reaction mixture with a functional group of a polymeric support to form a polymer-supported O-linked heteroaromatic N-oxide;
   b) adding a nucleophile to said reaction mixture; and
   c) reacting said nucleophile with said polymer-supported O-linked heteroaromatic N-oxide, thereby forming a substituted N-heteroaromatic compound.

2. The method of claim 1, wherein the polymeric support is insoluble.

3. The method of claim 1, wherein the polymeric support is soluble.

4. The method of claim 3, wherein the polymeric support comprises polyethylene glycol.

5. The method of claim 1, wherein the functional group of a polymeric support is an acid halide.

6. The method of claim 5, wherein the acid halide is an acid chloride.

7. The method of claim 1, wherein the functional group of a polymeric support is a sulfonyl halide.

8. The method of claim 1, wherein the functional group of a polymeric support is a phosphoryl halide.

9. The method of claim 1, wherein the functional group of a polymeric support is a benzyl halide.

10. The method of claim 1, wherein prior to the reacting step, the method includes the further step of purifying the O-linked heteroaromatic N-oxide.

11. The method of claim 1, wherein the heteroaromatic N-oxide is represented by the formula:

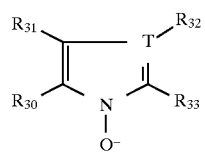

wherein
T is N or C;

$R_{30}$, $R_{31}$, $R_{32}$, and $R_{33}$ are independently selected from the group consisting of hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or $R_{30}$ and $R_{31}$ taken together form a carbocycle or heterocycle having from 4 to 10 atoms in the ring;

with the proviso that if T is N, $R_{32}$ is alkyl, aralkyl, or aryl.

12. The method of claim 1, wherein the heteroaromatic N-oxide is represented by the formula:

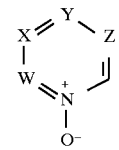

wherein
W, X, Y, and Z are each independently selected from the group consisting of N and $CR_1$, wherein each $R_1$ is independently selected from the group consisting of hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two $R_1$ taken together form a carbocycle or heterocycle having from 4 to 10 atoms in the ring structure.

13. The method of claim 12, wherein the heteroaromatic N-oxide is represented by the formula:

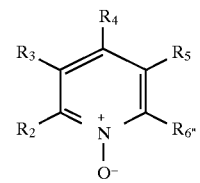

wherein $R_2$, $R_3$, $R_4$, $R_5$ and $R_{6''}$ each independently represent hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two of $R_2$, $R_3$, $R_4$, $R_5$ and $R_{6''}$ taken together form a carbocycle or heterocycle having from 4 to 10 atoms in the ring structure;

with the proviso that at least one of $R_2$, $R_4$, and $R_6$ is hydrogen.

14. The method of claim 13, wherein the heteroaromatic N-oxide is represented by the formula:

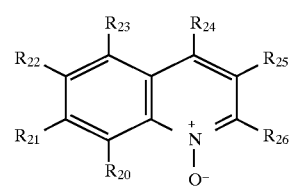

wherein $R_{20}$, $R_{21}$, $R_{22}$, $R_{23}$, $R_{24}$, $R_{25}$ and $R_{26}$ each independently represent hydrogen, halogen, alkyl, alkenyl, alkynyl, alkoxy, amino, carbonyl, cyano, thiol, thioalkoxy, aryl, amido, hydroxyl, carbamoyl, nitro, and trifluoromethyl, or any two of $R_{20}$, $R_{21}$, $R_{22}$, $R_{23}$, $R_{24}$, $R_{25}$ and $R_{26}$ taken together form a carbocycle or heterocycle having from 4 to 10 atoms in the ring structure;

with the proviso that at least one of $R_{21}$, $R_{23}$, $R_{24}$ and $R_{26}$ is hydrogen.

15. The method of claim 1, wherein the nucleophile is represented by the formula:

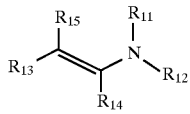

wherein $R_{11}$ and $R_{12}$ each independently represent alkyl, cycloalkyl, alkenyl, —$(CH_2)_m$—$R_7$, wherein $R_7$ represents aryl, cycloalkyl, cycloalkenyl, heterocyclyl or polycyclyl; and m is zero or an integer in the range of 1 to 8; or $R_{11}$ and $R_{12}$ taken together with the N atom to which they are attached complete a heterocycle having 5 or 6 atoms in the ring structure; and $R_{13}$, $R_{14}$ and $R_{15}$ each independently represent hydrogen, alkyl, cycloalkyl, alkenyl, or —$(CH_2)_m$—$R_7$; or $R_{13}$ and $R_{14}$ taken together with the ethylidene moiety to which they are attached complete a ring having from 4 to 8 atoms in the ring structure; or $R_{11}$ and $R_{15}$, taken together with the N atom and ethylidene moiety to which they are respectively attached, complete a heterocycle having from 4 to 8 atoms in the ring structure.

16. The method of claim 15, wherein the nucleophile is an indole.

17. The method of claim 15, wherein the nucleophile is an aromatic amine.

18. The method of claim 1, wherein the nucleophile is selected from the group consisting of thiols, cyanide, amines, alkoxides, acetylides, hydroxide, and stabilized carbanions.

19. A method of synthesizing a compound represented by the formula

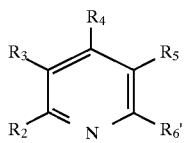

wherein $R_2$, $R_3$, $R_4$, and $R_5$ each independently represent hydrogen, halogen, alkyl, alkenyl, alkynyl, alkoxy, amino, carbonyl, cyano, sulfhydryl, alkylthio, aryl, amido, hydroxyl, carbamoyl, nitro, and trifluoromethyl; or any two or more of $R_2$, $R_3$, $R_4$, and $R_5$ taken together form a carbocycle or heterocycle having from 4 to 10 atoms in the ring structure; and $R_{6'}$ is a nucleophile adduct;

the method comprising:

a) reacting a heteroaromatic N-oxide represented by the formula:

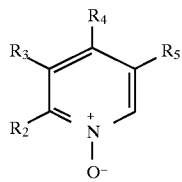

wherein $R_2$, $R_3$, $R_4$, and $R_5$ are as defined above;

with a functional group of a polymeric support in a reaction mixture to form a polymer-supported O-linked heteroaromatic N-oxide;

b) adding a nucleophile to said reaction mixture; and c) reacting said nucleophile with said polymer-supported O-linked heteroaromatic N-oxide, thereby forming a substituted N-heteroaromatic compound.

20. A method for synthesizing a library of substituted N-heteroaromatic compounds, the method comprising:

a) reacting a heteroaromatic N-oxide with a functional group of a polymeric support to form a polymer-supported O-linked heteroaromatic N-oxide; and b) reacting a nucleophile with said polymer-supported O-linked heteroaromatic N-oxide to form a library of substituted N-heteroaromatic compounds;

wherein at least one of said heteroaromatic N-oxide and said nucleophile is provided as a variegated population.

21. A method for synthesizing a library of substituted N-heteroaromatic compounds represented by the formula:

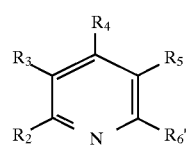

wherein $R_2$, $R_3$, $R_4$, and $R_5$ each independently represent hydrogen, halogen, alkyl, alkenyl, alkynyl, alkoxy, amino, carbonyl, cyano, sulthydryl, alkylthio, aryl, amido, hydroxyl, carbamoyl, nitro, and trifluoromethyl; or any two or more of the substituents taken together form a carbocycle or heterocycle having from 4 to 10 atoms in the ring structure; and $R_{6'}$ is a nucleophile adduct;

the method comprising:

a) reacting a heteroaromatic N-oxide represented by the formula

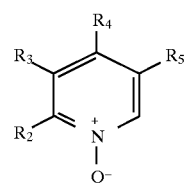

wherein $R_2$, $R_3$, $R_4$, and $R_5$ are as defined above;

with a functional group of a polymeric support to form an O-linked heteroaromatic N-oxide; and b) reacting a nucleophile with said O-linked heteroaromatic N-oxide to form a library of substituted N-heteroaromatic compounds;

wherein at least one of said heteroaromatic N-oxide and said nucleophile is provided as a variegated population.

* * * * *